US00PP34671P2

(12) United States Plant Patent
van der Arend

(10) Patent No.: US PP34,671 P2
(45) Date of Patent: Oct. 18, 2022

(54) ***PHILODENDRON* PLANT NAMED 'PPIPHFB014'**

(50) Latin Name: *Philodendron hybrida*
Varietal Denomination: PPIPHFB014

(71) Applicant: Rene P. A. van der Arend, Naaldwijk (NL)

(72) Inventor: Rene P. A. van der Arend, Naaldwijk (NL)

(73) Assignee: PLANT PLANET INTERNATIONAL B.V., Naaldwijk (NL)

( * ) Notice: Subject to any disclaimer, the term of this patent is extended or adjusted under 35 U.S.C. 154(b) by 0 days.

(21) Appl. No.: 17/545,700

(22) Filed: Dec. 8, 2021

(51) Int. Cl.
*A01H 5/12* (2018.01)
*A01H 6/10* (2018.01)

(52) U.S. Cl.
USPC ..... Plt./381

(58) Field of Classification Search
USPC ..... Plt./381
CPC ... A01H 5/12; A01H 5/00; A01H 5/02; A01H 6/10; A01H 6/00; A01H 1/121
See application file for complete search history.

(56) References Cited

U.S. PATENT DOCUMENTS

PP5,355 P * 11/1984 McColley ..... Plt./381

OTHER PUBLICATIONS

Etsy, retrieved on Feb. 7, 2022, retrieved from the Internet at https://www.etsy.com/listing/1076109007/rare-philodendron-florida-bronze-aerial?click_key=83a4a446716ce0e59ff4eff630d48420ef70f745%3A1076109007&click_sum=c92b25a1&ref=sold_out-6&frs=1&sts=1, 11pp. (Year: 2022).*

Cpvo Register 4.1.26 2022, retrieved on Feb. 9, 2022, retrieved from the internet at https://online.plantvarieties.eu/public-ConsultationDetails?registerId=20203090&denomination=ppiphfb014, 3 pp. (Year: 2022).*

* cited by examiner

*Primary Examiner* — June Hwu
(74) *Attorney, Agent, or Firm* — C. Anne Whealy

(57) ABSTRACT

A new and distinct cultivar of *Philodendron* plant named 'PPIPHFB014', characterized by its upright to outwardly spreading plant habit; moderately vigorous to vigorous growth habit; and hastate-shaped leaves that are initially reddish brown in color and becoming dark green with development.

2 Drawing Sheets

Figure 1:
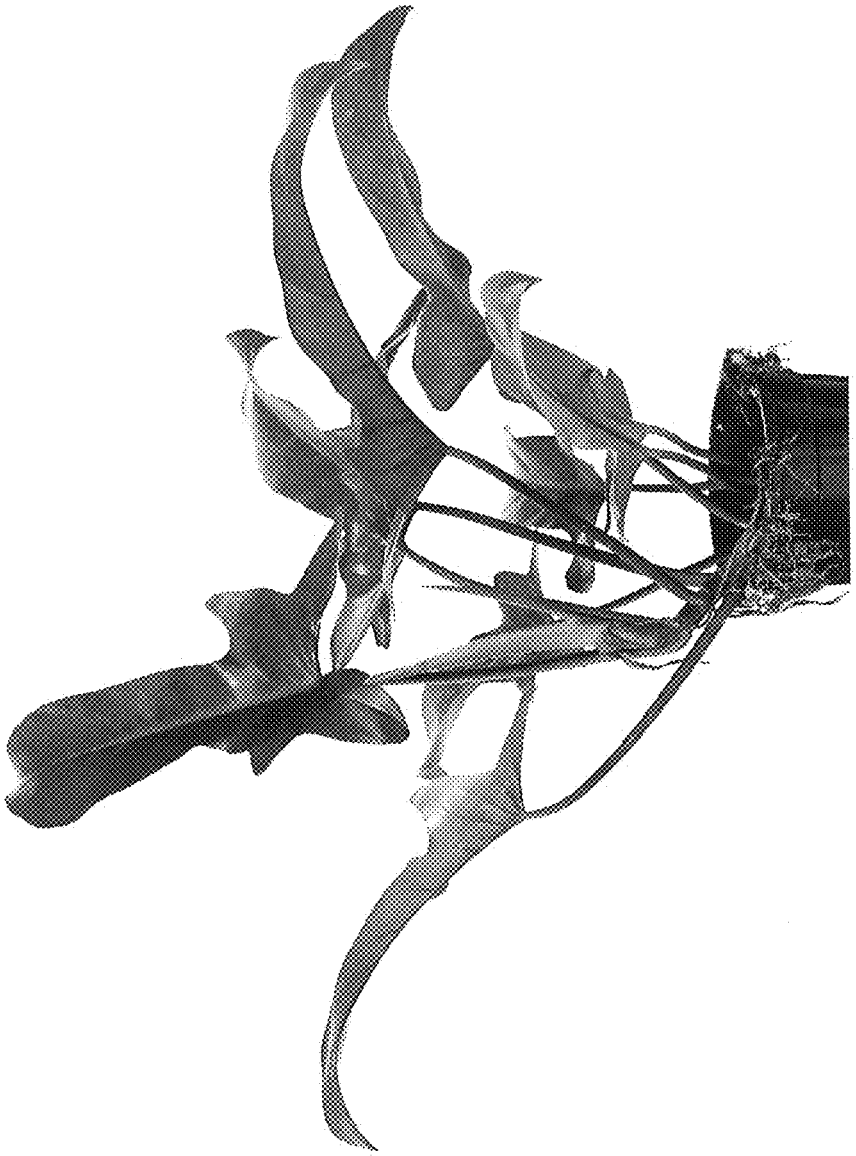

Botanical designation: *Philodendron hybrida.*
Cultivar denomination: 'PPIPHFB014'.

CROSS-REFERENCED TO A RELATED APPLICATION & STATEMENT REGARDING PRIOR DISCLOSURES BY INVENTOR/APPLICANT AND ASSIGNEE

This application does not claim priority to a European Community Plant Breeders' Rights application filed on Nov. 30, 2020, application number 2020/3090 and published on Feb. 15, 2021. There have been no offers for sale anywhere in the world prior to the effective filing date of this Application and no accessibility to one of ordinary skill in the art could have been derived from the printed Plant Breeder's Rights documents.

The Inventor/Applicant and Assignee assert that no publications nor advertisements relating to sales, offers for sale or public distribution occurred more than one year prior to the effective filing date of this application. Any information about the claimed plant would have been obtained from a direct or indirect disclosure from the Inventor/Applicant and/or Assignee. Inventor/Applicant claims a prior art exception under 35 U.S.C. 102(b)(1) for disclosure and/or sales prior to the filing date but less than one year prior to the effective filing date.

BACKGROUND OF THE INVENTION

The present invention relates to a new and distinct cultivar of *Philodendron* plant, botanically known as *Philodendron hybrida* and hereinafter referred to by the name 'PPIPHFB014'.

The new *Philodendron* plant is a product of a planned breeding program conducted by the Inventor in Naaldwijk, The Netherlands. The objective of the breeding program was to create new *Philodendron* plants with unique and attractive foliage coloration.

The new *Philodendron* plant originated from a cross-pollination conducted by the Inventor in Naaldwijk, The Netherlands in June, 2018 of *Philodendron hybrida* 'Florida Green', not patented, as the female, or seed, parent and *Philodendron hybrida* 'Black Cardinal', disclosed in U.S. Plant Pat. No. 5,355, as the male, or pollen, parent. The new *Philodendron* plant was discovered and selected by the Inventor as a single plant from within the progeny of the stated cross-pollination grown in a controlled greenhouse environment in Naaldwijk, The Netherlands in September, 2018.

Asexual reproduction of the new *Philodendron* plant by terminal cuttings in a controlled environment in Naaldwijk, The Netherlands since September, 2019 has shown that the unique features of this new *Philodendron* plant are stable and reproduced true to type in successive generations of asexual reproduction.

SUMMARY OF THE INVENTION

Plants of the new *Philodendron* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'PPIPHFB014'. These characteristics in combination distinguish 'PPIPHFB014' as a new and distinct *Philodendron* plant:

1. Upright to outwardly spreading plant habit.
2. Moderately vigorous to vigorous growth habit.
3. Hastate-shaped leaves that are initially reddish brown in color and becoming dark green with development.

Plants of the new *Philodendron* differ from plants of the female parent, 'Florida Green', primarily in leaf color as developing leaves of plants of the new *Philodendron* are reddish brown in color whereas developing leaves of plants of 'Florida Green' are green in color.

Plants of the new *Philodendron* differ from plants of the male parent, 'Black Cardinal', primarily in leaf color as developing leaves of plants of the new *Philodendron* are reddish brown and fully expanded leaves are dark green in color whereas developing leaves of plants of 'Black Cardinal' are burgundy red and fully expanded leaves are blackish green in color. In addition, leaves of plants of the new *Philodendron* are hastate in shape whereas leaves of 'Black Cardinal' are broadly oval in shape.

Plants of the new *Philodendron* can be compared to plants of an unnamed selection of *Philodendron squamiferum* known to the Inventor, not patented. Plants of the new *Philodendron* differ from plants of the unnamed selection of *Philodendron squamiferum* in the following characteristics:

1. Developing leaves of plants of the new *Philodendron* are reddish brown in color whereas developing leaves of plants of the unnamed selection of *Philodendron squamiferum* are green in color.
2. Stems of plants of the new *Philodendron* are smooth and glabrous whereas stems of plants of the unnamed selection of *Philodendron squamiferum* are pubescent.

BRIEF DESCRIPTION OF THE PHOTOGRAPHS

The accompanying photographs illustrate the overall appearance of the new *Philodendron* plant showing the colors as true as it is reasonably possible to obtain in colored reproductions of this type. Colors in the photographs may differ slightly from the color values cited in the detailed botanical description which accurately describe the colors of the new *Philodendron* plant.

The photograph on the first sheet (FIG. 1) is a side perspective view of a typical plant of 'PPIPHFB014' grown in a container.

Figure 2:
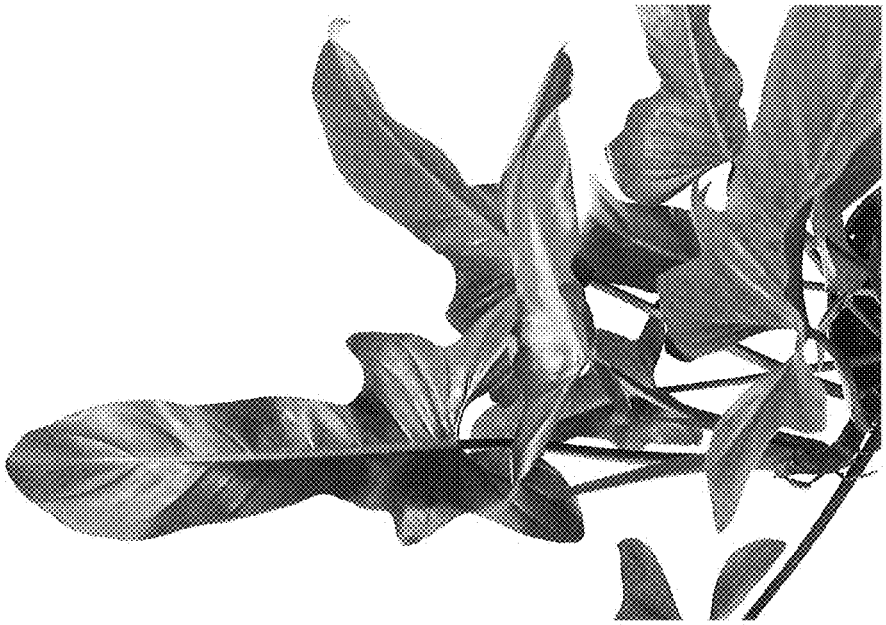

The photograph on the left of the second sheet (FIG. 2) is a close-up view of typical developing leaves of 'PPIPHFB014'.

Figure 3:
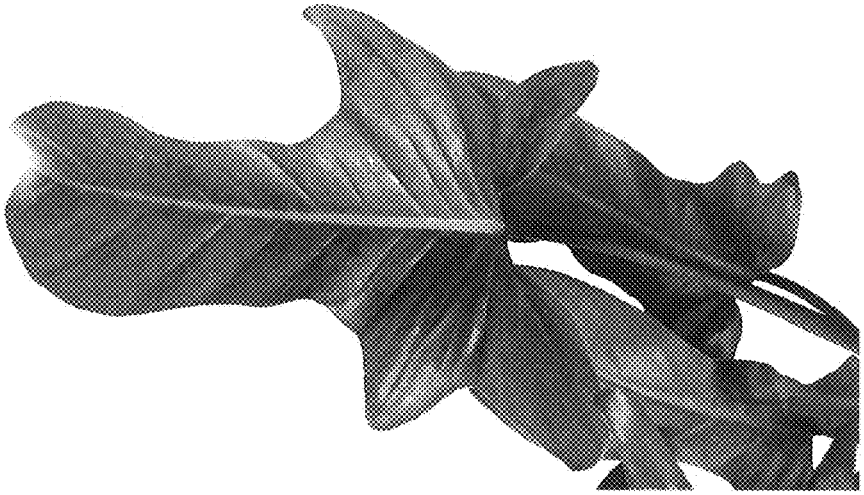

The photograph on the right of the second sheet (FIG. 3) is a close-up view of typical fully expanded leaves of 'PPIPHFB014'.

DETAILED BOTANICAL DESCRIPTION

The aforementioned photographs and following observations and measurements describe plants grown during the late summer and early autumn in 17-cm containers in a glass-covered greenhouse in Naaldwijk, The Netherlands and under cultural practices typical of commercial *Philodendron* production. During the production of the plants, day temperatures ranged from 10° C. to 25° C. and night temperatures ranged from 4° C. to 15° C. Plants were one year old when the photographs and the detailed description were taken. In the following description, color references are made to The Royal Horticultural Society Colour Chart, 2015 Edition, except where general terms of ordinary dictionary significance are used.

Botanical classification: *Philodendron hybrida* 'PPIPHFB014'.

Parentage:

*Female, or seed, parent.*—*Philodendron hybrida* 'Florida Green', not patented.

*Male, or pollen, parent.*—*Philodendron hybrida* 'Black Cardinal', disclosed in U.S. Plant Pat. No. 5,355.

Propagation:

*Type*.—By terminal cuttings.

*Time to initiate roots, summer*.—About 20 days at temperatures about 22° C. to 25° C.

*Time to initiate roots, winter*.—About 25 days at temperatures about 20° C. to 22° C.

*Time to produce a rooted young plant, summer*.—About 45 days at temperatures about 22° C. to 25° C.

*Time to produce a rooted young plant, winter*.—About 60 days at temperatures about 20° C. to 22° C.

*Root description*.—Fibrous, medium in thickness; typically white in color, actual color of the roots is dependent on substrate composition, water quality, fertilizers, substrate temperature and age of roots.

*Rooting habit*.—Moderately freely branching; medium density.

Plant description:

*Plant and growth habit*.—Upright to outwardly spreading plant habit; flattened globular in overall shape; moderately vigorous to vigorous growth habit and moderate growth rate.

*Plant height*.—About 39.5 cm.

*Plant diameter or spread*.—About 81.5 cm.

*Stem description*.—Branching habit: Plants of the new *Philodendron* typically have a single basal shoot; pinching will induce lateral branching. Length: About 14.3 cm. Diameter: About 1.6 cm. Internode length: About 2.1 cm. Aspect: Upright to about 55° from vertical. Strength: Strong. Texture and luster: Smooth, glabrous; glossy. Color, developing: Close to 181A. Color, developed: Close to N200A slightly tinged with close to 197A; at the internodes, close to between 165A and 165B.

Leaf description:

*Arrangement*.—Alternate; simple.

*Length*.—About 37.7 cm.

*Width*.—About 21.1 cm.

*Shape*.—Hastate with sagittate tendencies.

*Apex*.—Apiculate.

*Base*.—Hastate; lobes free.

*Margin*.—Entire; slightly and coarsely undulate.

*Lobing*.—If lobed, lobes are shallow to medium in depth and sinuses are divergent.

*Texture and luster, upper surface*.—Smooth, glabrous; slightly velvety; slightly glossy.

*Texture and luster, lower surface*.—Smooth, glabrous; slightly to moderately glossy.

*Venation pattern*.—Pinnate.

*Color*.—Developing leaves, upper surface: Slightly more intense than between 165A and N199B. Developing leaves, lower surface: Close to between 164A and 165A; towards the margins, close to N172A. Fully expanded leaves, upper surface: Close to between NN137A and 147A; irregularly mottled with close to 146A; venation, close to 147B. Fully expanded leaves, lower surface: Close to between 152A and N199A; color becoming closer to 146C with subsequent development; venation, close to 200B.

*Petioles*.—Length: About 25.2 cm. Diameter: Proximally, about 1.1 cm and distally, close to 8 mm. Aspect: Initially erect and then outwardly leaning. Strength: Moderately strong; flexible. Texture and luster, upper and lower surface: Smooth, glabrous; slightly glossy. Color, upper surface: Close to 200A to slightly darker than 200A. Color, lower surface: Close to between N186C and 200B; distally, close to N186C.

*Leaf bracts*.—Arrangement: One at the base of each petiole. Length: About 21.8 cm. Width: About 4.5 cm. Shape: Lanceolate with narrowly obtuse apex, broadly cuneate base and entire margins. Color, upper surface: Close to 185A. Color, lower surface: Close to between 184A and 185B.

Inflorescence description: To date, inflorescence initiation and development has not been observed on plants of the new *Philodendron*.

Pathogen & pest resistance: To date, plants of the new *Philodendron* not been observed to be resistant to pathogens and pests common to *Philodendron* plants.

Temperature tolerance: Plants of the new *Philodendron* have been observed to tolerate temperatures ranging from about 8° C. to about 40° C. and to be suitable for USDA Hardiness Zones 11 to 13.

It is claimed:

1. A new and distinct *Philodendron* plant named 'PPIPHFB014' as illustrated and described.

* * * * *